(12) United States Patent
Escano

(10) Patent No.: US 6,475,166 B1
(45) Date of Patent: Nov. 5, 2002

(54) GUIDEWIRE PLACEMENT SYSTEM FOR DELIVERY OF AN ANEURYSM GRAFT LIMB

(75) Inventor: Arnold Escano, Santa Clara, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 28 days.

(21) Appl. No.: 09/641,783

(22) Filed: Aug. 18, 2000

(51) Int. Cl.[7] .................................................. A61B 5/00
(52) U.S. Cl. .......................................... 600/585; 623/1
(58) Field of Search .............................. 600/585, 434; 623/1, 11, 12; 606/194, 195

(56) References Cited

U.S. PATENT DOCUMENTS

| | | | |
|---|---|---|---|
| 4,685,473 A | * | 8/1987 | Karcher et al. ............. 600/585 |
| 5,131,407 A | * | 7/1992 | Ischinger et al. ........... 600/434 |
| 5,290,229 A | * | 3/1994 | Paskar ......................... 600/434 |
| 5,327,906 A | * | 7/1994 | Fideler ........................ 600/585 |
| 5,591,228 A | | 1/1997 | Edoga |
| 5,755,777 A | | 5/1998 | Chuter |
| 5,824,041 A | | 10/1998 | Lenker et al. |
| 5,824,044 A | | 10/1998 | Quiachon et al. |
| 5,843,158 A | | 12/1998 | Lenker et al. |
| 5,871,536 A | | 2/1999 | Lazarus |
| 5,916,263 A | | 6/1999 | Goicoechea et al. |
| 5,948,018 A | | 9/1999 | Dereume et al. |

* cited by examiner

*Primary Examiner*—Max Hindenburg
(74) *Attorney, Agent, or Firm*—Blakely, Sokoloff, Taylor & Zafman LLP

(57) ABSTRACT

The present invention provides a guidewire placement system for delivery of an aneurysm graft limb. The invention is directed toward placement of grafts in abdominal aortic aneurysms where delivery of a contra-lateral limb is heretofore particularly difficult. The present invention provides external tubing which may be steered along with guide tubing having wire loops at the distal end thereof. The design of the external tubing and the guide tubing allow a contra-lateral guidewire to be directed toward and placed within a graft of the aneurysm. This allows for subsequent placement of a contra-lateral limb in an efficient and minimally invasive manner.

44 Claims, 9 Drawing Sheets

GUIDEWIRE PLACEMENT SYSTEM FOR DELIVERY OF AN ANEURYSM GRAFT LIMB

FIELD OF THE INVENTION

The present invention relates to the placement of aneurysm grafts and the instruments necessary to accomplish such placement. In particular, the present invention provides a guide steering device having exposable wire loops and a steering system for placement of an aneurysm graft limb.

BACKGROUND OF THE INVENTION

As shown in FIG. 1, an abdominal aneurysm graft 80 is used to allow blood to bypass the site of an abdominal aortic aneurysm 61 and pass to iliac vascular branches 62 there from without obstruction or backflow. The abdominal aneurysm graft 80 has a main body 64 and is bifurcated into ipsilateral 66 and contra-lateral 67 limbs at its proximal end. The limbs (66, 67) are meant for placement within iliac vascular branches 62 which branch off from the abdominal aorta 69.

In the last several years, the field of minimally invasive surgery has grown exponentially. As a result, even stent and graft placement has been affected. Presently, placement of an abdominal aneurysm graft 80 is accomplished by way of a minimally invasive catheterization technique. A guidewire 68 is inserted through a patient's vasculature and eventually through an iliac vascular branch 62 to the site of the aortic aneurysm 61. A balloon catheter (not shown) equipped with a capsule containing the aneurysm graft to be placed is delivered to the site of the aneurysm via the guidewire 68. The balloon portion of the catheter and the capsule are separable in order to deploy the main body 64.

Once the main body 64 is deployed, the balloon portion of the catheter may be positioned within the deployed main body 64. The balloon may then be inflated in order to anchor the main body 64 against the walls of the abdominal aorta 69 above the iliac bifurcation 71. Surgical hooks (not shown) may be provided at an outer portion of the main body 64 to promote its anchoring against the walls of the abdominal aorta 69 during this inflation.

As the main body 64 is deployed, an ipsilateral limb 66 may be exposed as attached to the main body 64. If this is the case, only a contra-lateral limb 67 will need to be added to the main body 64 in order to complete bypass of the aortic aneurysm 61 through the opposite (i.e. contra-lateral) iliac vascular branch 62. On the other hand, if the ipsilateral limb 66 is not initially provided as attached to the main body 64, it may be desirable to add it once the main body 64 is secured within the aortic aneurysm 61. Again, placement of the ipsilateral limb 66 is necessary to complete bypass of the aortic aneurysm 61 via the iliac vascular branch 62 through which the catheter has initially been introduced to the site.

If complete bypass via iliac vascular branches 62 is desired at this point, there is still a need to attach at least one graft limb subsequent to deployment of the main body 64. As indicated above, placement of the ipsilateral limb 66 is accomplished by either providing the ipsilateral limb 66 simultaneously with the main body 64 or by subsequently advancing the ipsilateral limb 66 to the site of the main body 64 via the guidewire 68 which has already been delivered. However, neither of these options is available for placement of the contra-lateral limb 67. Rather, it is necessary to have a separate guide for a separate advancement of the contra-lateral limb 67 to the site of the main body 64.

Unfortunately, it is very difficult to reach an implanted main body 64 in order to guide and subsequently attach the contra-lateral limb 67. This is because the aortic aneurysm 61 has a width which is much greater than either of the iliac vascular branches 62. Thus, once a limb delivering mechanism, such as a catheter adapted therefore, is advanced through an iliac vascular branch 62 to the site of the aortic aneurysm 61, it must traverse the aortic aneurysm 61 in an unguided manner and enter the main body 64 in order to subsequently deliver the contra-lateral limb 67.

The difficulty associated with placement of a contra-lateral limb 67 has been addressed by simply blocking off one of the iliac vascular branches 62 and utilizing a graft which is equipped with only the ipsilateral limb 66. However, this requires a subsequent more invasive surgical procedure to place a femoro-femoral bypass between the iliac vascular branches 62 in order to redeliver a flow of blood to the blocked iliac branch, proximal (i.e. below) the aortic aneurysm 61. Thus, many of the advantages of minimally invasive surgery have been lost. Alternatively, a second guidewire may be inserted through a patient's vasculature distal of the aortic aneurysm 61 and through the main body 64. Thus, once the entire abdominal aneurysm graft 80 is deployed, a guidewire will be present through both iliac branches. One or both of these guidewires may be used to aid in subsequent placement of limbs (66, 67). However this is a more complex procedure which requires additional incisions above (or distal) the aortic aneurysm 61 for external maintenance of the additional guidewire and introduction of the abdominal aneurysm graft 80. Lastly, an abdominal aneurysm graft 80 may be used without limbs (66, 67) at all. However, such an abdominal aneurysm graft 80 is not highly stable and does not provide an efficient bypass.

Therefore, what is desired is a system for placement of a contra-lateral aneurysm graft limb in a minimally invasive manner via a minimal number of incisions. It may be desirable to develop a system capable of delivering a second guidewire to the site of an aneurysm to aid in subsequent placement of a graft limb without requiring additional incisions above (or distal) the aneurysm.

SUMMARY OF THE INVENTION

The present invention provides a guidewire placement system for delivery of an aneurysm graft limb. The system may include steerable external tubing with an advanced flexible region which may be directed by manipulation of a steering wire.

The guidewire placement system may include guide tubing. The guide tubing is equipped with wire loops at a distal end thereof to promote accessibility of an aneurysm graft during guidewire placement.

The present invention also provides a method of providing a contra-lateral limb to a graft. The method may involve advancement of external tubing to the site of an aneurysm and graft while manipulating a steering wire which promotes movement of a distal extension of the external tubing toward a proximal contra-lateral portion of the graft.

The method may involve use of guide tubing. The guide tubing is advanced to the site of an aneurysm and graft where the tubing is further advanced into the graft followed by delivery of a guidewire.

The present invention provides a system for graft delivery to an aneurysm. The system may include a graft and a limb deployment catheter as well as means for advancing a contra-lateral guidewire into a placed graft.

DETAILED DESCRIPTION OF THE INVENTION

The following description makes reference to numerous specific details in order to provide a thorough understanding of the present invention. However each specific detail need not be employed to practice the present invention. Additionally, well-known details, such as particular materials or methods, have not been described in order to avoid unnecessarily obscuring the present invention.

Aneurysm graft placement is accomplished by way of a catheter which houses an aneurysm graft. Limbs which extend from the graft into arterial branches are often difficult to manipulate and in need of stable placement.

Figure 1:
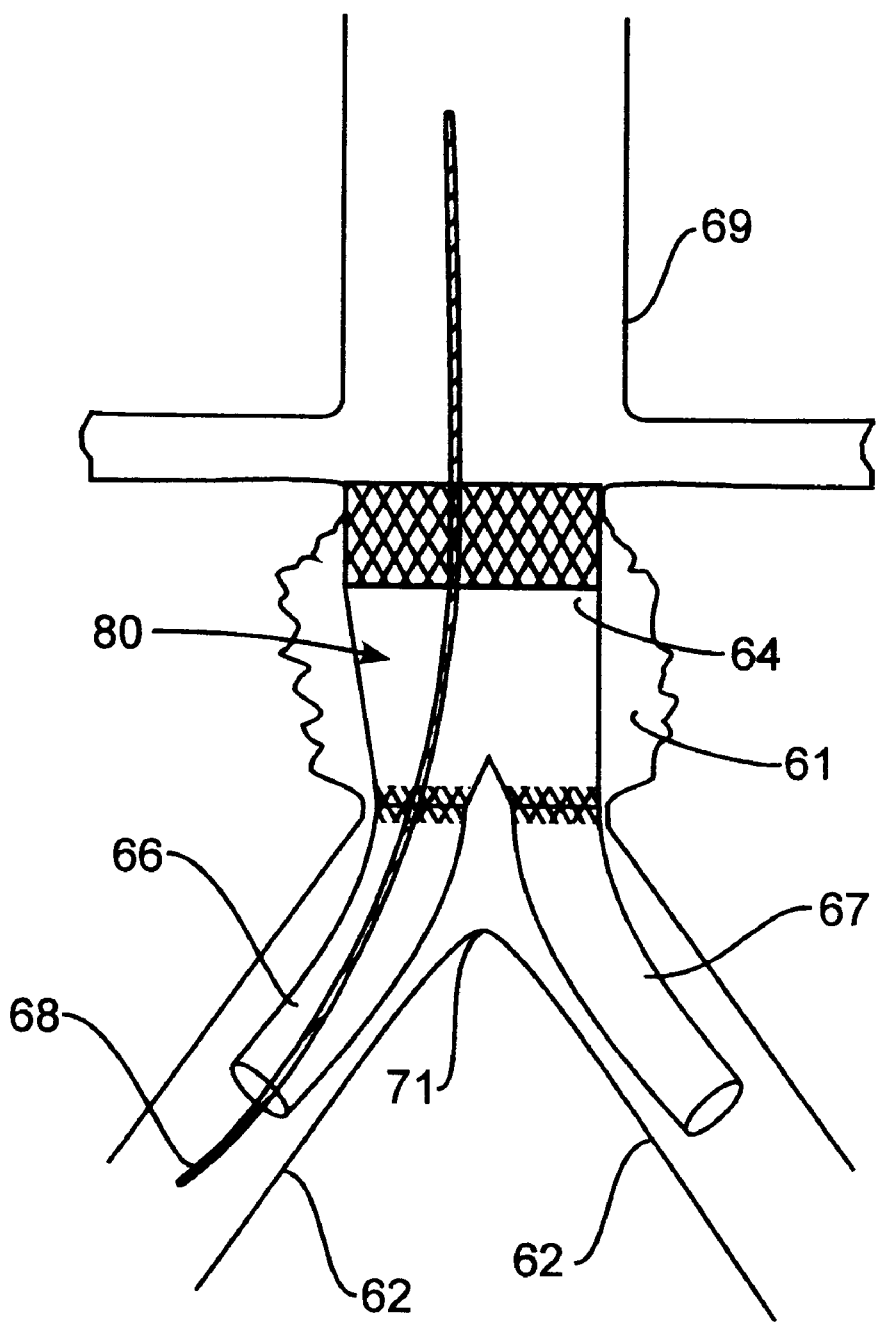
FIG. 1 is a cross section view of an abdominal aneurysm graft of the prior art.
Figure 2:
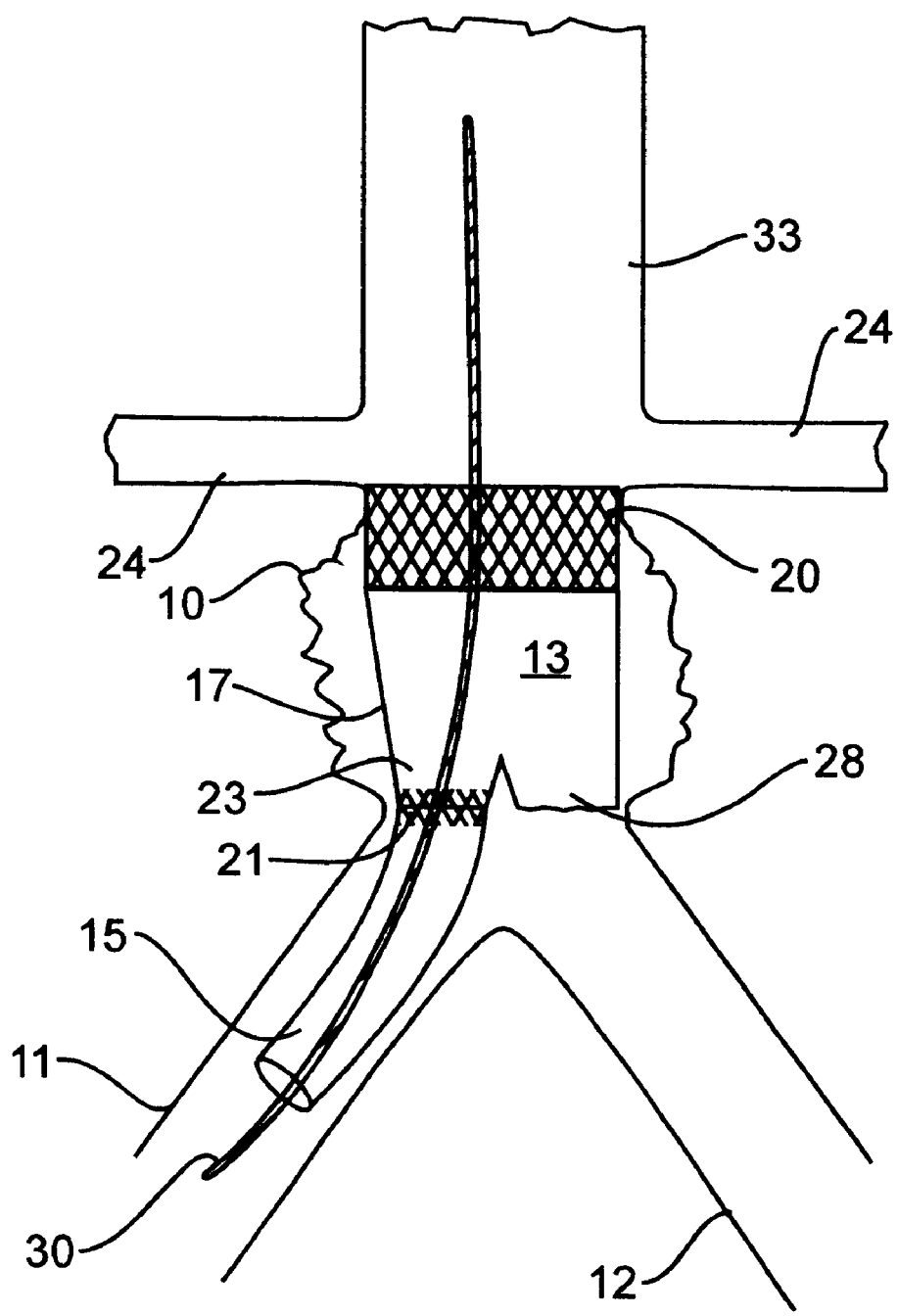
FIG. 2 is a cross sectional view of an abdominal aortic aneurysm having a graft deployed therein.

Referring to FIG. 2, an abdominal aneurysm 10 is shown. A graft 13 has been deployed within the abdominal aneurysm 10. An ipsilateral extension limb 15 is shown extending from a main body 17 of the graft 13. The ipsilateral extension limb 15 may have been attached to and deployed simultaneous with the main body 17. Alternatively, the ipsilateral extension limb 15 may be separately advanced to the main body 17 of the graft 13 via the ipsilateral guidewire 30.

The graft 13 is equipped with an anchoring region 20 having hooks (not shown) capable of circumferentially anchoring the graft 13 above the site of the aneurysm 10. The anchoring region 20 is disposed above the aneurysm 10 and below renal arteries 24. The ipsilateral extension limb 15 may have an attachment region 21 equipped with small hooks (not shown) capable of circumferentially attaching the ipsilateral limb 15 to a proximal ipsilateral portion 23 of the main body 17. However, small hooks will not be necessary where the ipsilateral extension limb 15 has been attached to and deployed simultaneously with the main body 17.

As shown in FIG. 2, a graft 13 has been delivered to the site of an abdominal aneurysm 10 with a bypass of the ipsilateral iliac artery 11 complete. This degree of bypass may be completed by advancement of such a graft 13 and ipsilateral limb 15 simultaneously to the site of the aneurysm 10 with a graft deployment balloon catheter capable of delivering such (not shown). Alternatively, this degree of bypass maybe completed by advancement of the ipsilateral limb 15 subsequent to the delivery of the main body 17. The graft deployment balloon catheter is advanced to the site of the aneurysm 10 by way of an ipsilateral guidewire 30. The ipsilateral guidewire 30 has been advanced to the site of the aneurysm 10 and into the aorta 33 via a femoral portion of the ipsilateral iliac artery 11.

A balloon of the graft deployment balloon catheter (not shown) may aid in the placement of the graft 13 and ipsilateral limb 15. That is, the balloon may be positioned within the main body 17, inflated, and advanced proximally to within the ipsilateral limb 15. This inflation and advancement forces open the main body 17 and the ipsilateral limb 15 and helps secure these features in place.

If the ipsilateral limb 15 is to be delivered and deployed separate from the graft 13, this may be done by a separate advancement of a limb deployment balloon catheter (not shown) along the same ipsilateral guidewire 30. Such a separate delivery and deployment may be desirable in order to maintain a low profile and ease advancement of the graft deployment balloon catheter. That is, the graft deployment balloon catheter would have less to deliver and thus be capable of having a smaller diameter, which would ease its advancement through the ipsilateral iliac artery 11.

As shown in FIG. 2, bypass of the aneurysm 10 is not complete. In order to complete the bypass, a contra-lateral limb 16 (see FIG. 6) must still be delivered to the graft 13 and into the contra-lateral iliac artery 12.

Figure 3:
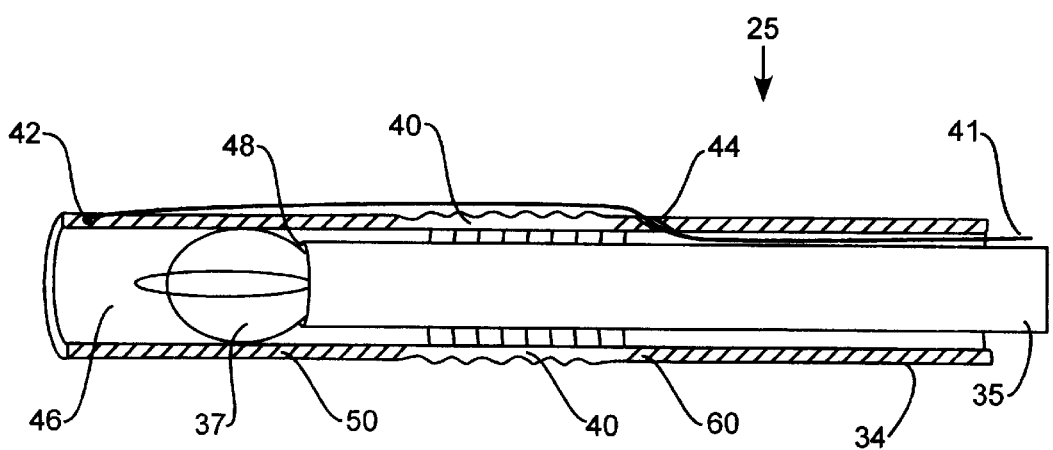
FIG. 3 is a side sectional view of the steerable guidewire system of one embodiment of the present invention.

FIG. 3 reveals a side sectional view of the steerable guidewire placement system 25 of one embodiment of the present invention. The guidewire placement system 25 is capable of delivering a contra-lateral guidewire 26 to a proximal contra-lateral portion 28 of the graft 13 is shown (see also FIG. 6). Delivery of this contra-lateral guidewire 26 allows subsequent advancement of a limb deployment balloon catheter (not shown) to the graft 13 and deployment of a contra-lateral limb 16 thereat (see also FIG. 6). The proximal contra-lateral portion 28 may have a length different from that of the proximal ipsilateral portion 23. Different lengths of the proximal portions (28, 23) may be desired for various reasons such as for ease of packing of the graft 13 prior to deployment.

The guidewire placement system 25 is equipped with external tubing 34. In one embodiment, the external tubing 34 has a diameter in a range of approximately 0.120 to 0.156 inches and has a length of approximately 112 centimeters. The external tubing 34 may be of a thermoplastic elastomer resin such as PEBAX®.

The guidewire placement system 25 may also include an advanced flexible region 40. The advanced flexible region 40 may be located near the distal end of the external tubing 34. The advanced flexible region 40 is more flexible than its immediately surrounding portions of the external tubing 34. The advanced flexible region 40 may be a portion of the external tubing 34 which utilizes a compression spring in place of PEBAX® or a like material which makes up surrounding portions of the external tubing 34. In one embodiment, a compression spring having about five coils may be used. The advanced flexible region 40 may have an accordion configuration. In another embodiment, the advanced flexible region 40 may be a thinner portion of the external tubing 34 (i.e. in comparison to proximal tubing 60 proximal thereto), with or without a compression spring disposed therein. In yet another embodiment, the advanced flexible region 40 may have a diameter in the range of approximately 0.021 to 0.206 inches and a length of approximately 0.940 inches long.

Steering wire 41 is provided to the external tubing 34. The steering wire 41 may be stainless steel or a nickel titanium alloy (commercially referred to as "nitinol"). In one embodiment, the diameter of the steering wire 41 may be in a range of approximately 0.010 and 0.014 inches in diameter. This range of diameter allows for visualization via fluoroscopy during a surgical procedure and avoids kinking of the wire 41. The steering wire 41 is secured at an attachment site 42 distal of the advanced flexible region 40. The portion of the external tubing 34, distal of the advanced flexible region 40, is referred to here as the distal extension 50.

The attachment site 42 may simply be a hole or a post through, or about, which the steering wire 41 may be secured. Additionally, the attachment site 42 may be a location at which the steering wire 41 has been bonded to the external tubing 34, with or without use of an adhesive. A wire channel 44 is present through the external tubing 34 at a location proximal the advanced flexible region 40. The steering wire 41 is external to the external tubing 34 between the attachment site 42 and the wire channel 44.

The steering wire 41 is threaded through the wire channel 44 and travels proximally within the external tubing 34, eventually exiting the external tubing 34 at a proximal end thereof where it may be manipulated by a physician. That is, the physician's manipulation of the steering wire 41 at a proximal end thereof is capable of causing the external tubing 34 to bend at the advanced flexible region 40. The distal extension 50 is the portion of the external tubing 34 which moves as the advanced flexible region 40 bends in response to the physician's manipulation of the steering wire 41. Placement of the attachment site 42 and the wire channel 44 as indicated focuses the force resulting from the manipulation of the steering wire 41 on the advanced flexible region 40 causing it to bend in this manner.

The external tubing 34 of FIG. 3 is shown cross sectioned and enveloping guide tubing 35. The guide tubing 35 may allow the external tubing 34 to enter the main body 17 (see FIG. 4D). The guide tubing 35, having a guide lumen 48 there through may be made of various materials such as a thermoplastic elastomer or a high density polyethylene (HDPE). The guide tubing 35 may have a diameter in the range of approximately 0.050 to 0.080 inches and a length of approximately 160 centimeters. The guide tubing 35 is capable of lateral movement within the external tubing 34.

Wire loops 37 are disposed at the distal end of the guide tubing 35. The wire loops 37 may again be stainless steel or nitinol wire having a diameter in the range of approximately 0.010 to 0.014 inches in diameter. The wire loops 37 may include loops set perpendicular to one another. The wire loops 37 may play a significant role in advancement of the external tubing 34 to within the main body 17 (see also FIG. 4D).

Figure 4A:
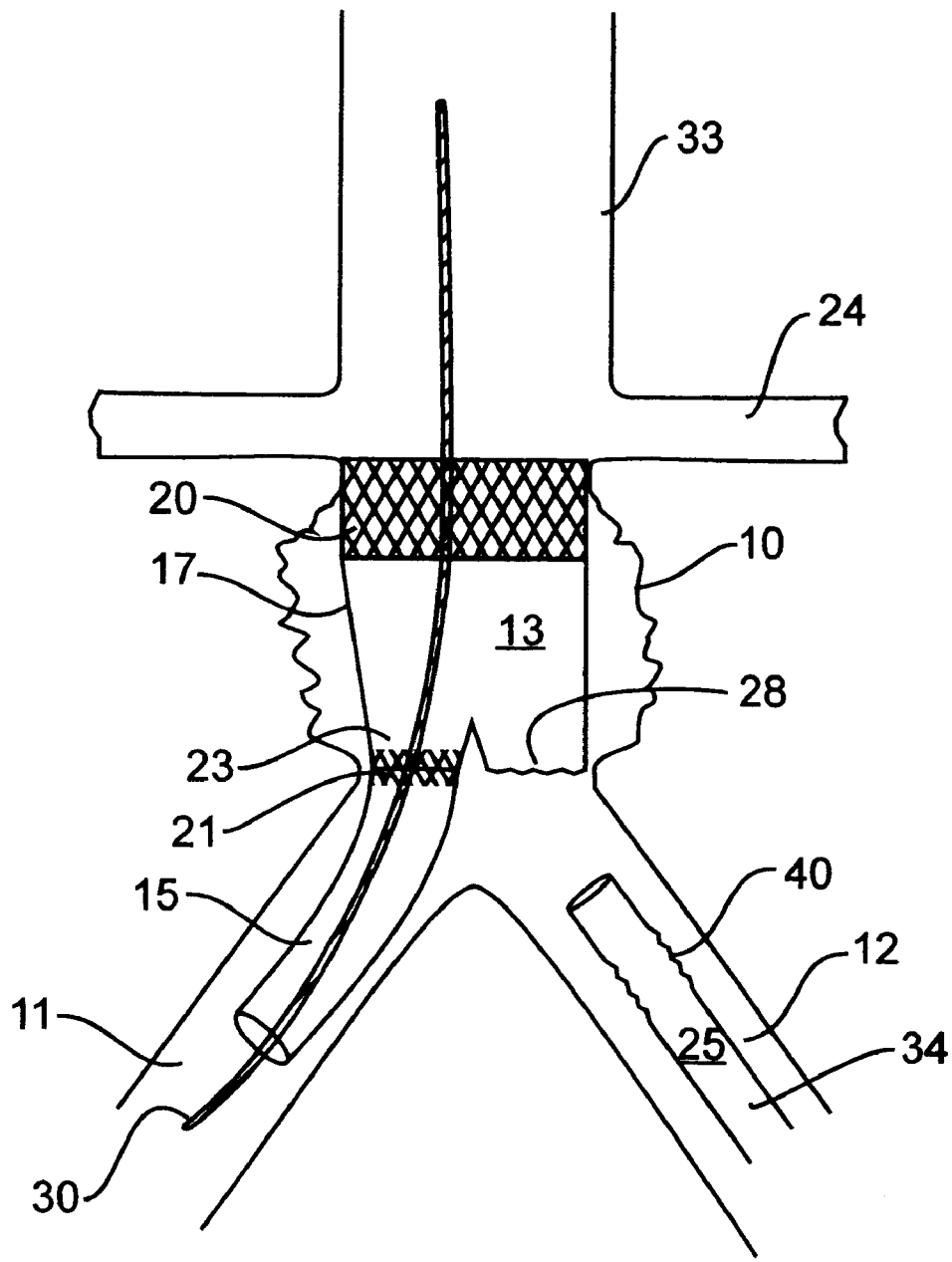
FIG. 4A is a cross sectional view of an abdominal aortic aneurysm having a graft deployed therein and the steerable guidewire system of the present invention.

FIGS. 4A–4D and 5 illustrate how the guidewire placement system 25 may be used. As shown in FIG. 4A, the external tubing 34 is inserted through a femoral artery and advanced through the contra-lateral iliac artery 12 to the site of the abdominal aneurysm 10. In one embodiment the external tubing 34 is advanced to this position it may be equipped with a filling wire (not shown) to block off its guidewire lumen 46 (see FIG. 3). Filling wire may be used to prevent accumulation of blood and bodily fluids within the guidewire placement system 25 and may also help avoid accidental coring of vasculature as the guidewire placement system 25 is advanced. Alternatively, the guide tubing 35 maybe present within the guidewire lumen 46 during insertion (see FIG. 3). However, in such a situation, the loops 37 should be kept entirely within the guidewire lumen 46 during insertion in order to prevent damage to vasculature as the guidewire placement system 25 is advanced.

Figure 4B:
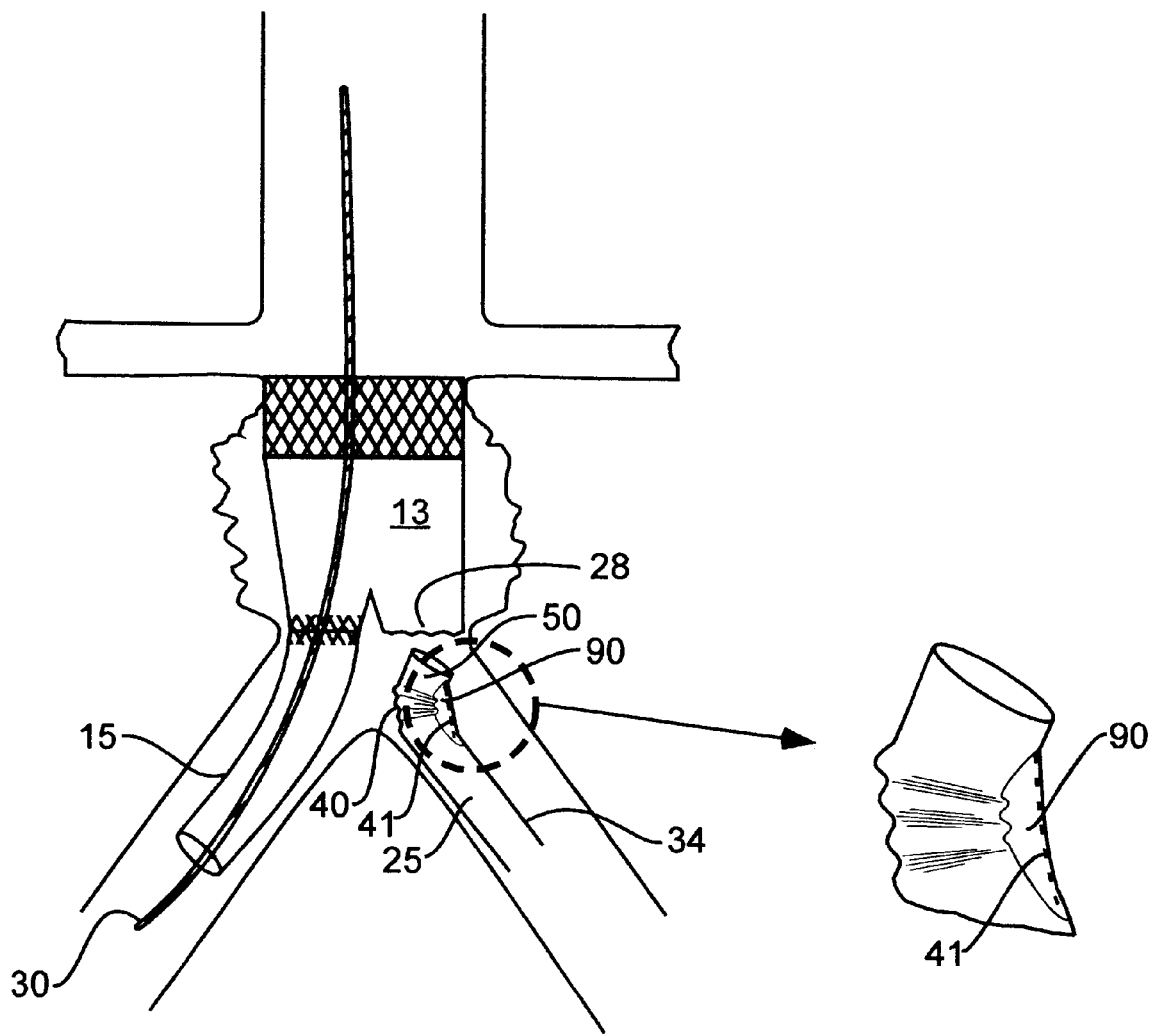
FIG. 4B is a cross sectional view of an abdominal aortic aneurysm having a graft deployed therein and the steerable guidewire system of the present invention.

The goal of the guidewire placement system 25 is to reach the proximal contra-lateral portion 28 of the graft 13 so that a contra-lateral guidewire 26 may be delivered. Referring to FIG. 4B, a manner of steering the external tubing 34 is shown. This steering capability enhances the ability of the external tubing 34 to reach the proximal contra-lateral portion 28 of the graft 13. Without steering (or wire loops 37) it is very difficult for the physician to direct the external tubing 34 to the precise location of the proximal contra-lateral portion 28.

Steering is accomplished by the physician's manipulation of the steering wire 41 which acts to create an angle at the advanced flexible region 40 of the external tubing. Additionally, the physician has the ability to control the direction of the angle at the advanced flexible region 40 by rotating the external tubing 34 at a proximal end thereof. Thus, if the physician's manipulation of the steering wire 41 has caused the distal extension 50 to bend toward the ipsilateral limb 15 in an undesired manner, the external tubing 34 may be rotated to cause the distal extension 50 to point toward the proximal contra-lateral portion 28 as desired.

For safety, a protective drape 90 may be provided over the steering wire 41. The protective drape 90 would tightly attach to the external tubing 34 on each side of the steering wire 41. The protective drape 90 may also be attached to the external tubing 34 distal the attachment site 42 and proximal the wire channel 44 (see also FIG. 3). The protective drape 90 would be flexible enough to allow flexure of the advanced flexible region 40 and loose enough to allow the external tubing 34 to remain un-flexed if desired. The protective drape 90 encases the steering wire 41 between the external tubing 34 and the protective drape 90. This helps prevent damage to surrounding vasculature by a possibly otherwise exposed and unprotected steering wire 41.

A lock (not shown) may be provided proximal of the advanced flexible region 40. Use of the lock allows the physician to release the steering wire 41 without causing a change in the bent angle of the advanced flexible region 40. That is, once the physician has bent the external tubing 34 to a desired angle at the advanced flexible region 40, the lock may be used to secure the angle. Securing the angle allows the physician to release the steering wire 41 and concentrate efforts elsewhere.

Figure 4C:
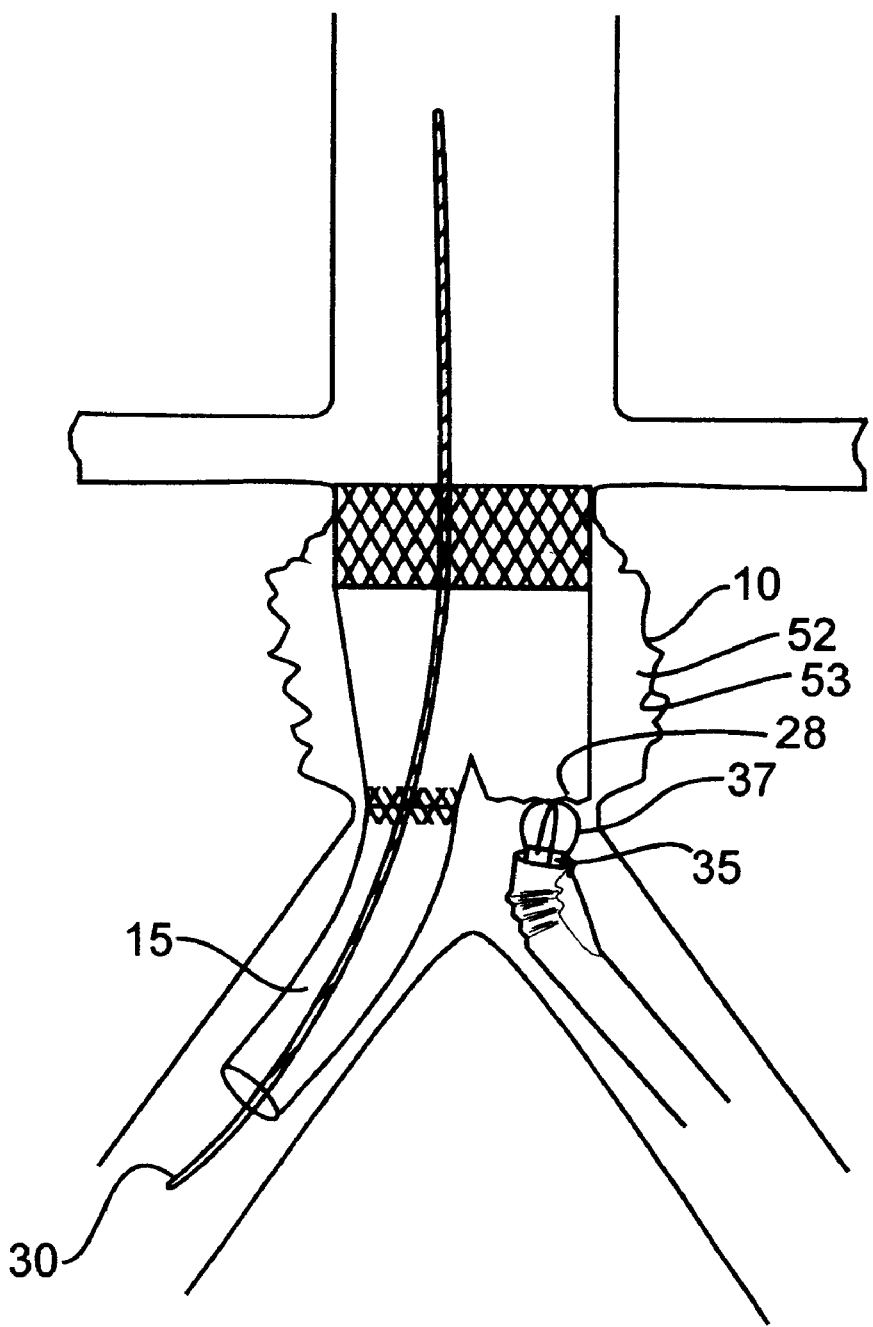
FIG. 4C is a cross sectional view of an abdominal aortic aneurysm having a graft deployed therein and the steerable guidewire system of the present invention with guide tubing being deployed.

Referring to FIG. 4C, another manner of enhancing the ability of the external tubing 34 to reach the proximal contra-lateral portion 28 of the graft 13, is shown. Once the guidewire placement system 25 has been advanced into the aneurysm body 52, any filling wire (not shown) will be removed, and replaced with guide tubing 35, if not already present. The guide tubing 35 may be advanced distally forcing the wire loops 37 out of the guidewire lumen 46 and exposing them to the aneurysm body 52. The wire loops 37 aid the advancement of the external tubing 34 into the proximal contra-lateral portion 28 in two ways. The wire loops 37 may come into contact with the wall 53 of the aneurysm 10 and prevent the guide tubing 35 from doing the same. Thus, the guide tubing 35 is kept relatively centered within the aneurysm body 52 (i.e. and in closer proximity to the proximal contra-lateral portion 28). The wire loops 37 are capable of catching and holding open the proximal contra-lateral portion 28. Rotating the guide tubing 35 at a proximal end thereof may enhance this capability. The rotation of the guide tubing 35 may cause a rotation of the wire loops 35 and thus, encourage their entry into the proximal contra-lateral portion 28.

Figure 4D:
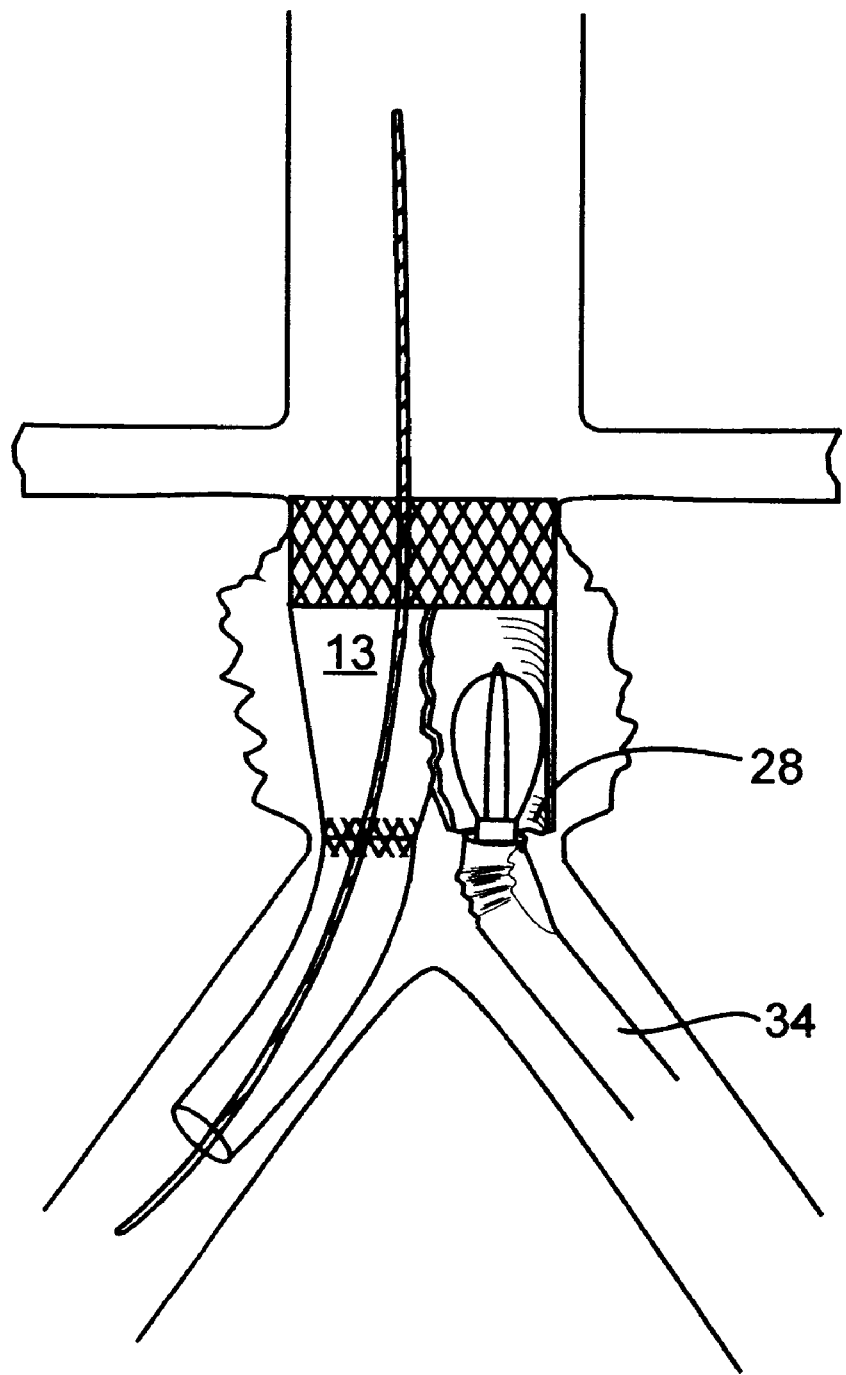
FIG. 4D is a cross sectional view of an abdominal aortic aneurysm and a graft deployed therein with an exposed steerable guidewire system.

Referring to FIG. 4D, a partial cross sectional view of the graft 13 is shown such that the inside of the proximal contra-lateral portion 28 can be seen. The wire loops 37 are shown within the proximal contra-lateral portion 28. The wire loops 37 keep the proximal contra-lateral portion 28 open and not collapsed. Thus, the external tubing 34 may easily be advanced into the proximal contra-lateral portion 28.

Figure 5:
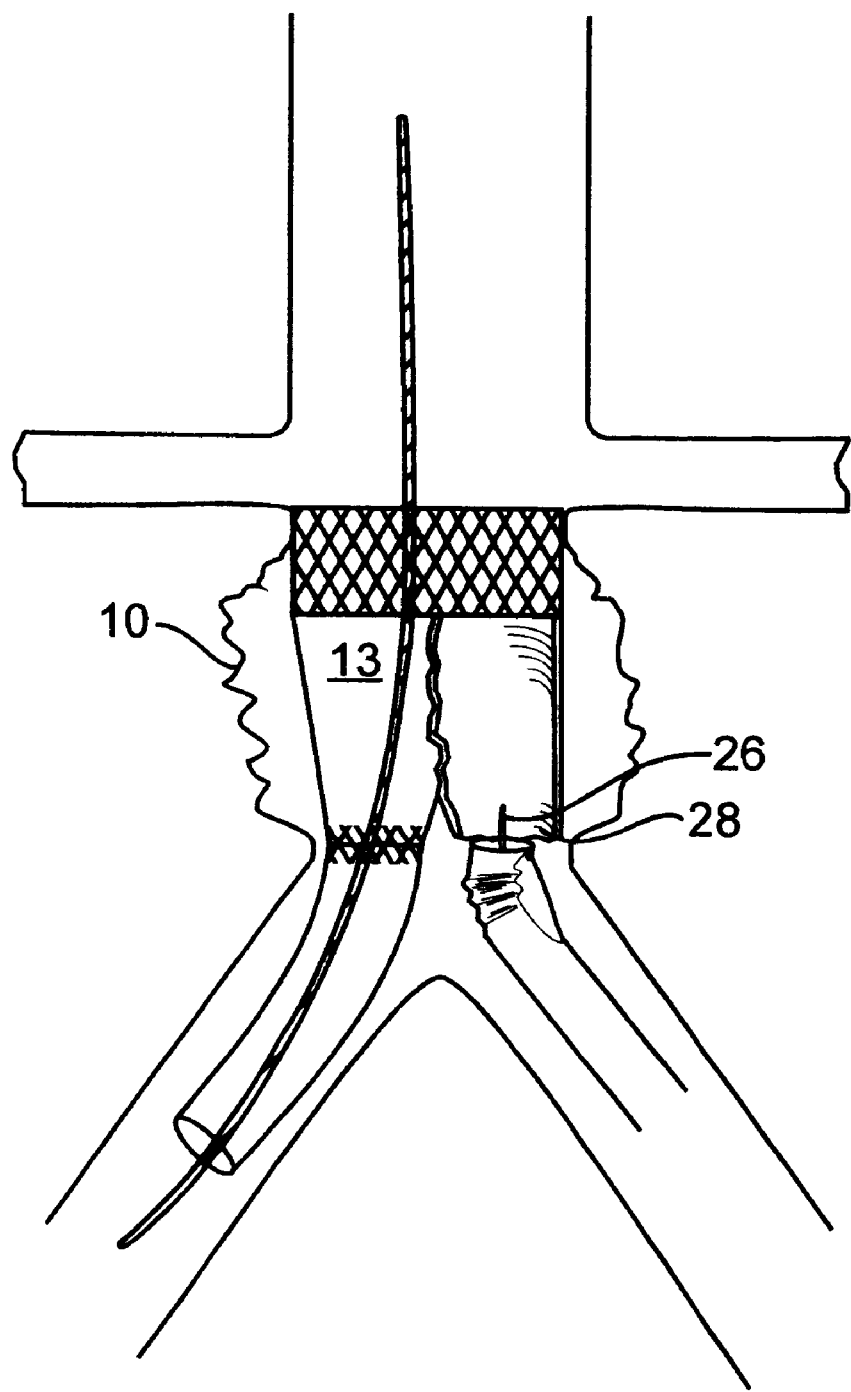
FIG. 5 is a cross sectional view of an abdominal aortic aneurysm and a graft deployed therein with a guidewire having been advanced through a steerable guidewire system.

Referring to FIG. 5, another partial cross sectional view of the graft is shown such that the inside of the proximal contra-lateral portion 28 may be seen. Once the external tubing 34 has been advanced to within the proximal contra-lateral portion 28 the guide tubing 35 may be removed. The external tubing 34 may then be used as a conduit for advancing a contra-lateral guidewire 26. The contra-lateral guidewire 26 may have a diameter of approximately 0.035 inches. The external tubing 34, directs the contra-lateral guidewire 26 safely to the graft 13. The guide tubing 35 (see FIG. 4D) has been replaced with the contra-lateral guidewire 26. The contra-lateral guidewire 26 has been delivered within the contra-lateral portion of the graft 13.

Figure 6:
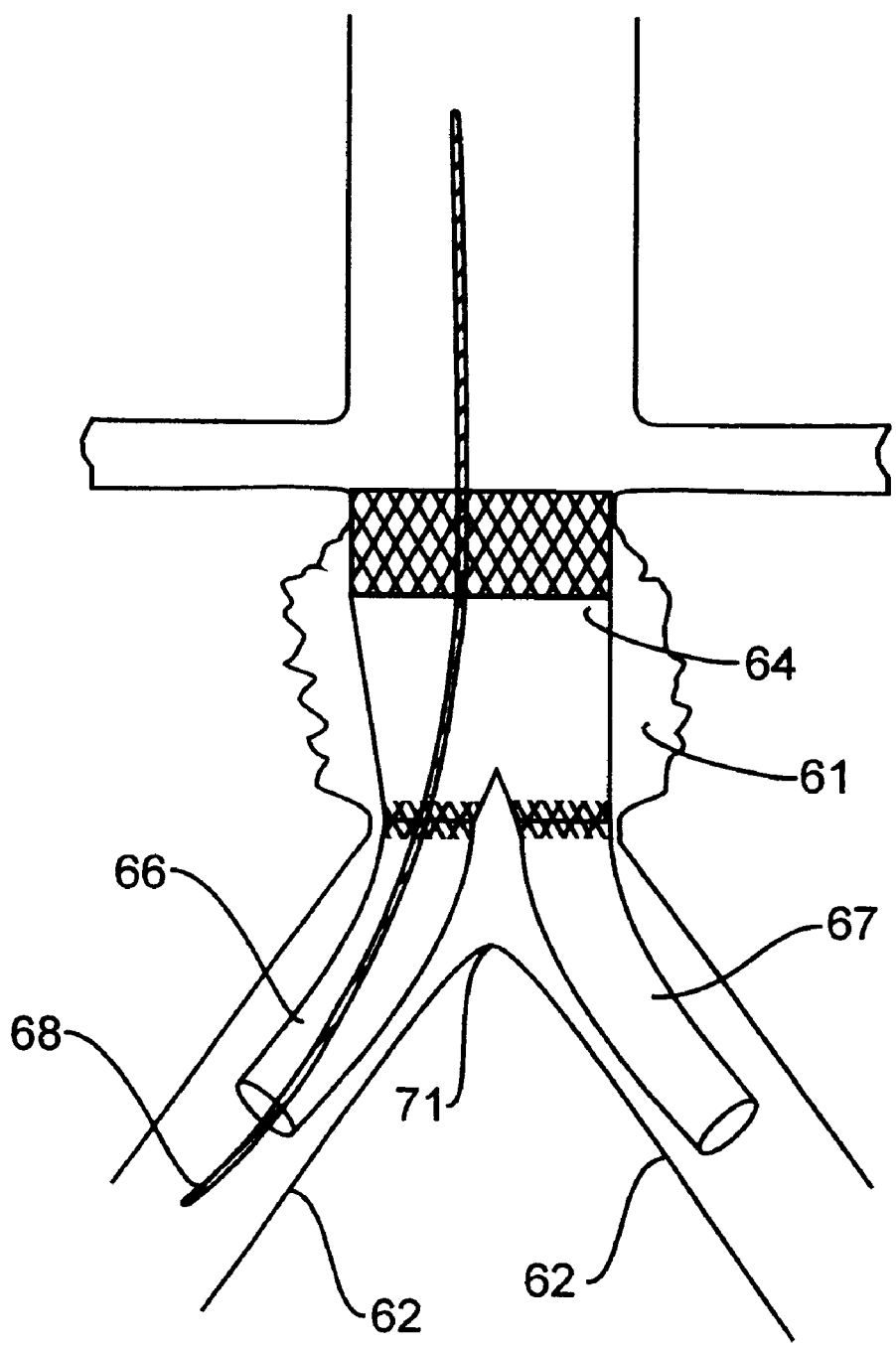
FIG. 6 is a cross sectional view of an abdominal aortic aneurysm having a graft deployed therein with extension limbs running therefrom into iliac arteries.

Referring to FIG. 6, once a contra-lateral guidewire 26 is within the contra-lateral portion of the graft 13, a contra-lateral limb 16 may be delivered. The contra-lateral limb 16 may be delivered along with the contra-lateral guidewire 26 via conventional means such as with a balloon catheter (not shown) equipped with a capsule containing the contra-lateral limb 16. The contra-lateral limb 16 may have small hooks (not shown) at a distal region 70 for attachment to the proximal contra-lateral portion 28. Once the contra-lateral limb 16 is deployed, the graft 13 is complete within the abdominal aneurysm.

Although an exemplary embodiment of the invention has been shown and described in the form of a steerable and centering guidewire placement system, many changes, modifications, and substitutions may be made by one having ordinary skill in the art without necessarily departing from the spirit and scope of this invention. For example, the present invention would be applicable to any guidewire placement system in which the area for guidewire placement was difficult to access.

I claim:

1. An apparatus comprising:
    external tubing having a distal flexible region and a distal extension distal of said distal flexible region;
    steering wire secured to said distal extension to cause flexure of sid distal flexible region; and
    a protective drape about said steering wire and secured to said external tubing.

2. The apparatus of claim 1, wherein said external tubing comprises a thermoplastic elastomer resin.

3. The apparatus of claim 1, wherein said external tubing is of a diameter in the range of approximately 0.120 to 0.156 inches.

4. The apparatus of claim 1, wherein said external tubing further comprises proximal tubing, said proximal tubing proximal said distal flexible region, said distal flexible region thinner than said proximal tubing.

5. The apparatus of claim 4, wherein said distal flexible region includes a compression spring disposed therein.

6. The apparatus of claim 1, wherein said distal flexible region includes a compression spring.

7. The apparatus of claim 1, wherein said distal flexible region is of a diameter in a range of approximately 0.021 to 0.206 inches.

8. The apparatus of claim 1 wherein said distal flexible region has an accordion configuration.

9. The apparatus of claim 1 wherein said steering wire is of a material selected from the group consisting of nitinol and stainless steel.

10. The apparatus of claim 1 wherein said steering wire is in a range of approximately 0.010 to 0.014 inches in diameter.

11. The apparatus of claim 1 wherein said steering wire is secured to said distal extension at an attachment site of said distal extension, said attachment site comprising a hole through said distal extension.

12. The apparatus of claim 1 wherein said steering wire is secured to said distal extension at an attachment site of said distal extension, said attachment site comprising a post extending from said distal extension.

13. The apparatus of claim 1 further comprising a wire channel through a surface of said external tubing and into a lumen of said external tubing, said wire channel proximal of said distal extension, said steering wire secured to said distal extension at an exterior portion of said distal extension and traversing said surface via said wire channel.

14. The apparatus of claim 13 wherein said wire channel is proximal said distal flexible region.

15. A placement system comprising:
    guide tubing; and
    wire loops disposed at a distal end of said guide tubing, said wire loops promoting accessibility of a graft and avoidance of an aneurysm wall by said guide tubing when said guide tubing is present within an aneurysm having a graft disposed within said aneurysm.

16. The system of claim 15, wherein said guide tubing comprises a material selected from the group consisting of high density polyethylene and thermoplastic elastomer resin.

17. The system of claim 15, wherein said guide tubing is of a diameter in a range of approximately 0.050 to 0.080 inches.

18. The system of claim 15, wherein said wire loops are of a material selected from the group consisting of nitinol and stainless steel.

19. The system of claim 15, wherein said wire loops comprise wire having a diameter in a range of approximately 0.010 to 0.014 inches.

20. The system of claim 15, wherein said wire loops comprise a first wire loop positioned perpendicular to a second wire loop.

21. The system of claim 15 further comprising external tubing removably surrounding said wire loops to promote ease of advancement of said system through a body lumen.

22. The system of claim 21 wherein said external tubing may be steered by manipulation at a proximal end of said external tubing.

23. A method of providing a contra-lateral limb to a graft at a site of an aneurysm, said method comprising:
    advancing external tubing through vasculature to the site of the aneurysm, said external tubing having an advanced flexible region to flex via manipulation of a steering wire secured to said external tubing at a distal portion of said external tubing;
    manipulating said steering wire in order to direct a distal extension of said external tubing toward a proximal contra-lateral portion of said graft;

inserting said external tubing into said graft through said proximal contra-lateral portion; and introducing a contra-lateral guidewire through a lumen of said external tubing and into said graft.

24. The method of claim 23 further comprising guiding a limb deployment balloon catheter having a contra-lateral limb disposed within said limb deployment balloon catheter to said graft at said aneurysm via said contra-lateral guidewire.

25. The method of claim 23 further comprising removing said external tubing after said introducing.

26. The method of claim 23 further comprising immobilizing said steering wire proximal of said advanced flexible region prior to said introducing in order to preserve a desired angle of said advanced flexible region.

27. The method of claim 23 further comprising rotating said external tubing to direct said distal extension toward said proximal contra-lateral portion after said advancing.

28. The method of claim 27 further comprising filling said lumen with a filling wire prior to said advancing.

29. A method of providing a contra-lateral limb to a graft at the site of an aneurysm, said method comprising:

advancing guide tubing through vasculature to the site of the aneurysm, said guide tubing having wire loops disposed at a distal end of said guide tubing, said wire loops promoting accessibility of said graft and avoidance of a wall of said aneurysm by said guide tubing;

inserting said guide tubing into said graft through a proximal contra-lateral portion of said graft; and introducing a contra-lateral guidewire to said graft through said proximal contra-lateral portion.

30. The method of claim 29 further comprising guiding a limb deployment balloon catheter having a contra-lateral limb disposed within said limb deployment balloon catheter to said graft at said aneurysm via said contra-lateral guidewire.

31. The method of claim 29 further comprising rotating said guide tubing prior to said inserting in order to promote said inserting.

32. The method of claim 29 further comprising removably surrounding said guide tubing and said wire loops with external tubing prior to said advancing.

33. The method of claim 32 wherein said introducing of said contra-lateral guidewire occurs through said external tubing.

34. The method of claim 32 further comprising withdrawing said external tubing to expose said wire loops prior to said inserting.

35. The method of claim 34 further comprising forcing said external tubing into said graft through said proximal contra-lateral portion after said inserting.

36. The method of claim 35 further comprising removing said guide tubing prior to said introducing.

37. A system for delivery of a graft to an aneurysm, said system comprising:

a graft deployment balloon catheter having said graft disposed therein and deliverable to said aneurysm via an ipsilateral guidewire;

a limb deployment balloon catheter having a contra-lateral limb disposed therein and deliverable to said aneurysm via a contra-lateral guidewire; and means for advancing said contra-lateral guidewire into said graft once said graft has been delivered to said aneurysm.

38. The system of claim 37 wherein said means comprises external tubing having an advanced flexible region to flex via manipulation of a steering wire secured to said external tubing at a distal portion of said external tubing.

39. The system of claim 37 wherein said means comprises guide tubing having wire loops disposed at a distal end of said guide tubing, said wire loops promoting accessibility of said graft and avoidance of a wall of said aneurysm by said guide tubing.

40. The system of claim 37 wherein said contra-lateral limb further comprises hooks, said hooks capable of securing said contra-lateral limb to a proximal contra-lateral portion of said graft once said graft has been delivered to said aneurysm.

41. The system of claim 37 wherein said graft has a main body and further comprises a proximal contra-lateral portion and a proximal ipsilateral portion.

42. The system of claim 37 wherein an ipsilateral extension limb is incorporated with said graft.

43. The system of claim 37 wherein said graft deployment balloon catheter is to accommodate an ipsilateral extension limb apart from said graft.

44. The system of claim 37 wherein said graft further comprises an anchoring region having hooks for securing said graft within said aneurysm.

* * * * *

UNITED STATES PATENT AND TRADEMARK OFFICE
CERTIFICATE OF CORRECTION

PATENT NO.    : 6,475,166 B1          Page 1 of 1
DATED         : November 5, 2002
INVENTOR(S)   : Escano It is certified that error appears in the above-identified patent and that said Letters Patent is hereby corrected as shown below:

Column 7,
Line 56, please delete "sid" and insert -- said --.

Signed and Sealed this

Twenty-eighth Day of October, 2003

JAMES E. ROGAN
*Director of the United States Patent and Trademark Office*